(12) United States Patent
Ritter et al.

(10) Patent No.: US 6,505,062 B1
(45) Date of Patent: Jan. 7, 2003

(54) METHOD FOR LOCATING MAGNETIC IMPLANT BY SOURCE FIELD

(75) Inventors: Rogers C. Ritter, Charlottesville, VA (US); Bevil J. Hogg, Town & Country, MO (US); Peter R. Werp, Los Gatos, CA (US); Francis M. Creighton, IV, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 372 days.

(21) Appl. No.: 09/020,942

(22) Filed: Feb. 9, 1998

(51) Int. Cl.[7] ................................................ A61B 5/00
(52) U.S. Cl. ........................ 600/407; 600/424; 128/899
(58) Field of Search ............................... 600/424, 407; 128/899; 606/108; 340/686; 361/143

(56) References Cited

U.S. PATENT DOCUMENTS

| | | | |
|---|---|---|---|
| 3,358,676 A | 12/1967 | Frei | 128/1.3 |
| 3,674,014 A | 7/1972 | Tillander | 128/2.05 R |
| 5,093,754 A | 3/1992 | Kawashima | 361/144 |
| 5,125,888 A | 6/1992 | Howard et al. | 600/12 |
| 5,332,987 A | 7/1994 | Hennessy et al. | 335/216 |
| 5,334,207 A | 8/1994 | Gay, Jr. | 606/7 |
| 5,353,807 A | 10/1994 | DeMarco | 128/772 |
| 5,523,684 A | 6/1996 | Zimmermann | 324/207.22 |
| 5,558,091 A | 9/1996 | Acker et al. | 128/653.1 |
| 5,654,864 A | 8/1997 | Ritter et al. | 361/141 |
| 5,794,569 A | * 8/1998 | Titus et al. | 119/721 |

OTHER PUBLICATIONS

"Characteristics of an Improved Magnetic–Implant Guidance System," Robert G. McNeil at al., IEEE Trans. Biomed. Eng., vol. 42, No. 8, Aug. 1995, pp. 802–808.

"Functional Design Features and Initial Performance Characteristics of a Magnetic–Implant Guidance Systems for Stereotactic Neurosurgery," Robert G. McNeil et al., IEEE Trans. Biomed. Eng., vol. 42, No. 8, Aug. 1995, pp. 793–801.

"Magnetic Manipulation Instrumentation for Medical Physics Research," G.T. Gillies et al., Rev. Sci. Instrum. 65 (3); Mar. 1994, pp. 533–562.

"Goniometric Motion Controller for the Superconducting Coil in a Magnetic Stereotaxis System," Elizabeth G. Quate et al., IEEE Trans. Biomed. Eng., vol. 38, No. 9, Sep. 1991, pp. 899–905.

"Nonlinear magnetic stereotaxis: Three–dimensional, in vivo remote magnetic manipulation of a small object in canine brain," M.S. Grady et al., Med. Phys. 17 (3), May/Jun. 1990, pp. 405–415.

(List continued on next page.)

*Primary Examiner*—Ruth S. Smith
(74) *Attorney, Agent, or Firm*—Harness, Dickey & Pierce, P.L.C.

(57) ABSTRACT

An apparatus and method for locating a magnetic implant in a surgical application using the field of a source magnet for the implant guiding field. The source magnet is an electromagnet having a separate calibrated magnetic field component in addition to the guiding field, so that both the magnitude and orientation of the magnetic field as a function of position around the magnet are known. A magnetic implant is provided with a sensor, such as a three-axis Hall effect sensor, to provide an indication of the magnitude and orientation of an applied magnetic field when the implant is surgically implanted in a patient. After implantation, the source magnet is energized with a current having a modulated component. The modulated component is received and filtered from the signal received from the Hall effect sensor in the implant, and provided to a processor that computes the location of the implant relative to the electromagnet based upon the detected magnitude and orientation of the modulated component of the magnetic field, and the location and orientation of the electromagnet. Localizers may be used to supply the relative locations of the patient and the electromagnet to the processor. A display may be provided to display a representation of the location of the implant in the patient, which may also be superimposed over a preoperative image of the patient.

5 Claims, 1 Drawing Sheet

OTHER PUBLICATIONS

"External Magnetic Guidance of Endovascular Catheters With a Superconducting Magnet: Preliminary Trials," A. Gaston et al., J. Neuroradiol 1988, 15, pp. 137–147.

A review of medical application of magnet attractions and detection, Jack Driller et al., Journal of Med. Eng. & Tech., vol. 11, No. 6, Nov./Dec. 1987, pp. 271–277.

"A Rotating D.C. Superconducting Magnet System for Guidance of Intravascular Catheters," S.R. Savitz et al., $28^{th}$ ACEMB, Sep. 20–24, 1975, p. 422.

"Magnetically Guided Devices for Vascular Exploration and Treatment," Sadek K. Hilal et al., Radiology 113, Dec. 1974, pp. 529–540.

"Laboratory experience with a magnetically guided intravascular catheter system," Herbert L. Cares et al., J. Neurosurg., vol. 38, Feb. 1973, pp. 145–154.

"Kinetics of Magnetically Guided Catheters," Jack Driller, IEEE Transactions on Magnetics, vol. MAG–6, No. 3, Sep. 1970, pp. 467–471.

"Selective Angiography with a Catheter Guided by a Magnet," H. Tillander, IEEE Transactions on Magnetics, vol. MAG–6, No. 2, June 1970, pp. 355–358.

"The POD Bronchial Catheter," Jack Driller et al., IEEE Transactions on Magnetics, vol. MAG–6, No. 2, Jun. 1970, pp. 353–355.

"The POD Bronchial Catheter and Associated Biopsy Wire," Med. & biol. Engng., vol. 8, 1970, pp. 15–18.

"Selective Cerebral Catheterization," Jonathan Molcho et al., IEEE Trans. Bio. Med. Eng., vol. BME–17, No. 2, Apr. 1970, pp. 134–140.

"Magnetism and Medicine," E.H. Frei, Journal of Applied Physics, vol. 40, No. 3, Mar. 1969, pp. 955–957.

"The Magnetically Guided Bronchial Catheter of Modified POD Design," William J. Casarella et al., Radiology (93), Oct. 1969, pp. 930–932.

"Development and Use of the POD Catheter in the Cerebral Vascular System," J. Driller et al., Medical Research Engineering, Aug.–Sep. 1969, pp. 11–16.

"Superconducting Magnet System for Intravascular Navigation," D.B. Montgomery et al., Journal of Applied Physics, vol. 40, No. 5, Apr. 1969, pp. 2129–2132.

"POD Catheter: A Means for Small Vessel Exploration," S.K. Hilal et al., Journal of Applied Physics, vol. 40, No. 3, Mar. 1969, p. 1046.

"A New Magnet System For 'Intravascular Navigation'," Shyam B. Yodh et al., Med. And Bio. Eng., vol. 6, 1968, pp. 143–147.

"Magnetically controlled intravascular catheter," John F. Alksne, Surgery, vol. 64, No. 1, Jul., 1968, pp. 339–345.

"The Pod and its Applications," Frei et al., p. 65, Proceedings of the Annual Conference on Engineering in Medicine and Biology, San Francisco, CA, 1966.

"Development of the 'Pod' and Experiments on Dogs," Frei et al., pp. 89, Proceedings of the 17th Annual Conference on Engineering in Medicine and Biology, Cleveland, OH,, Nov. 16–18, 1964.

"The 'Pod', a New Magnetic Device for Medical Application," E.H. Frei et al., pp. 156–157, Proceedings of the $16^{th}$ Annual Conference on Engineering in Medicine and Biology, Baltimore, M.D., Nov. 18–20, 1963.

"Magnetic Guidance of a Catheter With Articulated Steel Tip," Hans Tillander, Acta Radiologia (35), Jan. 1951, pp. 62–64.

* cited by examiner

METHOD FOR LOCATING MAGNETIC IMPLANT BY SOURCE FIELD

BACKGROUND OF THE INVENTION (1) Field of the Invention

This invention relates to methods for locating a magnetic implant, and more specifically, to a method for locating a magnetic object being guided, in a surgical application, by the field of a source magnet.

(2) Description of Related Art

In the field of surgery, there exists a need to control the orientation, forces, and/or motion of internally implanted devices. One method that has been used to control such implanted devices is the application of a magnetic field from an external magnet. In this method, the magnetic field acts upon the implanted device, which itself comprises magnetic material, which may be in the form of a permanent magnet. In accordance with prior art practice, a physician surgically implants the device comprising magnetic material and then guides the position of the implanted device by moving an external permanent magnet and observing the resultant movement directly with an X-ray fluoroscope. Examples of the prior art may be found in a review article by Gillies et al., "Magnetic Manipulation Instrumentation for Medical Physics Research," Rev. Sci. Instrum. 65, 533 (1994). See also McNeil et al., "Functional Design Features and Initial Performance Characteristics of a Magnetic-Implant Guidance System for Stereotactic Neurosurgery," IEEE Trans. Biomed. Engrg., 42, 793 (1995); Tillander, "Magnetic Guidance of a Catheter with Articulated Steel Tip," Acta Radiologa 35. 62 (1951); Frei et al, "The POD (Para-Operational Device) and its Applications," Med. Res. Eng. 5,11 (1966); U.S. Pat. No. 3,358,676 to Frei et al., issued Dec. 19, 1967, entitled "Magnetic Propulsion of Diagnostic or Therapeutic Elements Through the Body Ducts of Animal or Human Patients"; Hilal et al., "Magnetically Guided Devices for Vascular Exploration and Treatment," Radiology 113, 529 (1974); Yodh, et al., "A New Magnet System for Intravascular Navigation," Med. & Biol. Engrg., 6, 143 (1968); Montgomery et al., "Superconducting Magnet System for Intravascular Navigation," Jour. Apppl. Phys. 40, 2129 (1969); U.S. Pat. No. 3,674,014 to Tillander, issued Jul. 4, 1972, entitled "Magnetically Guidable Catheter-Tip and Method"; and U.S. Pat. No. 3,794,041 to Frei et al., issued Feb. 26, 1974, entitled "Gastrointestinal Catheter." The full content of each of the cited documents are herein incorporated by reference in their entirety.

Obviously, the above-described technique requires the physician to react to the movement of the implanted device. Determination of this movement can be a problem, because the implanted device can, in general, move in three-dimensional space inside the patient. With prior art hand-held magnets, the only feedback the surgeon could have was his observation of motion of a magnetic implant by x-ray or ultrasonic imaging in response to his movement of the magnet. Usually, fluoroscopic imaging is employed. However, fluoroscopic imaging can be subject to interference from the magnet, itself. In difficult interference situations, it is difficult without proper imaging guidance to provide even a reasonable guess as to a correct direction for the magnet axis to obtain field alignment with the intended path. The large electromagnet of Yodh et al. (supra) is one attempt to minimize the "blindness" of the approach just described, but the Yodh et al. approach still relies on operator judgment and vision, and is subject to such error.

While multiple coil arrangements such as the magnetic stereotaxis system (MSS) described in McNeil et al. (supra) can be used to provide:such guidance, it is difficult in such systems to provide a combined guiding force and force-applying field gradient in the same desired direction.

U.S. Pat. No. 5,558,091 issued Sep. 24, 1996 to Acker et al., which is hereby incorporated by reference in its entirety, discloses a magnetic position and orientation determining system using magnetic fields. By monitoring field components detected at a probe during application of the fields, the position and orientation of the probe in the field can be determined. A representation of the probe can be superimposed on a separately acquired image of the subject to show the position and orientation of the probe with respect to the subject. Although the devices and methods disclosed in this patent can determine the location of an implant, the magnetic fields used are so small as to not exert any significant, perceptible forces on magnetic materials in the sensing region. There is no disclosure or suggestion to use a magnetic field to both align and/or guide an implanted probe as well as determine its location via an externally applied magnetic field, nor is there any suggestion to place strongly magnetizable materials or permanent magnets in a seed or on a probe, adjacent to a magnetic sensor, in such a manner as to allow accurate determination of location using the magnetic sensor in the immediate vicinity of the seed.

Clearly, both operation time and risk to a patient could be reduced if an apparatus and method were available to more accurately and reliably locate, as well as guide, orient, and/or move a magnetic surgical implant. (For present purposes, when reference is made to "guiding" an implant, it should be assumed that this may also refer to "orienting" an implant, as well.) Preferably, while such apparatuses and methods may allow the use of x-ray, ultrasonic, or fluoroscopic imaging devices, they should not require such imaging devices to provide the location of the implant. In addition, it would be advantageous if the location method would not require the addition of magnetic field creating devices, such as is required by the Acker et al. patent, and which might further increase the interference with the location and operation of a guiding magnet. If the location can be obtained without the use of such additional imaging and/or locating devices, the external magnet or electromagnet (or magnets or electromagnets) used for guiding the magnetic implant may be provided with a larger, unobstructed range of motion. It would also be advantageous if the location can be obtained without being subject to interference from the magnet itself, as occurs or can occur with many common fluoroscopic imaging systems.

SUMMARY OF THE INVENTION

There is thus provided, in accordance with a first aspect of the invention, a magnetic surgical implant comprising a flexible probe having a magnetic seed mounted at a distal end thereof and a magnetic field sensor mounted near the magnetic seed and in a fixed relationship thereto so that as an external magnetic field acts on the magnetic seed to guide or propel it through a patient's body, the magnetic field sensor is also acted upon and provides an output that can be correlated with the position of the magnetic seed.

This embodiment of the invention may include a 3-axis magnetometer probe as the magnetic field sensor, which may be mounted within the flexible probe. Signals from the sensor may be conducted from the magnetic field sensor through the flexible probe by at least one sensor conductor. The probe itself may be a catheter or an endoscope.

There is also provided, in accordance with another aspect of the invention, a device for providing position data for a magnetic surgical implant having a magnetic field sensor which is guided or propelled through a patient's body by an external magnet, said device comprising a current source for supplying a modulated electrical current to the external magnet to thereby generate an oscillating magnetic field component, a demodulator coupled to the magnetic field sensor and responsive to a magnetic field direction and magnitude of the oscillating magnetic field component to provide a signal indicative of the oscillating magnetic field component at the location of the magnetic field sensor, a memory containing a representation of a relationship of spatial locations to a magnetic field pattern produced by the external magnet, and a data processor coupled to the demodulator and the memory and configured to compute a spatial location of the magnetic field sensor as a function of the signal indicative of the oscillating magnetic field component.

In accordance with yet another aspect of the invention, a method for locating a magnetic implant is provided, comprising the steps of (a) surgically implanting a magnetic implant including an associated magnetic probe in a patient; (b) applying a modulated magnetic field from an external electromagnet; (c) detecting signals from the magnetic probe resulting from the modulated magnetic field; and (d) calculating the relative location and orientation of the magnetic probe, and therefore, the magnetic implant, with respect to the electromagnet from the detected signals from the magnetic probe.

Additional steps to the above-described method may be added, in accordance with the invention. Such steps may include locating the patient and the electromagnet so that an indication of the magnetic probe, and therefore, the magnetic implant, is displayed. An additional step of superimposing this indication over a preoperative image of the patient may also be included.

It is thus an object of this invention to provide a method and apparatus for locating a magnetic object which is being guided by the field of a source magnet, using the field of the source magnet itself to locate the object.

It is a further object of this invention to provide a method and apparatus for accurately and reliably locating a magnetic surgical implant without requiring x-ray, ultrasonic, or fluoroscopic imaging devices.

It is another object of this invention to provide a method and apparatus for accurately and reliably locating a magnetic surgical implant by using a magnet that simultaneously serves the functions of guiding a magnetic implant and locating it.

It is yet a further object of the invention to provide a method and apparatus for locating a magnetic surgical implant that permits a wide range of unobstructed motion to be provided to an external magnet or electromagnet for guiding the magnetic surgical implant.

It is a still further object of the invention to provide a method and apparatus for locating a magnetic surgical implant that is not subject to interference caused by the presence of the external magnet.

DESCRIPTION OF THE PREFERRED EMBODIMENTS

Figure 1:
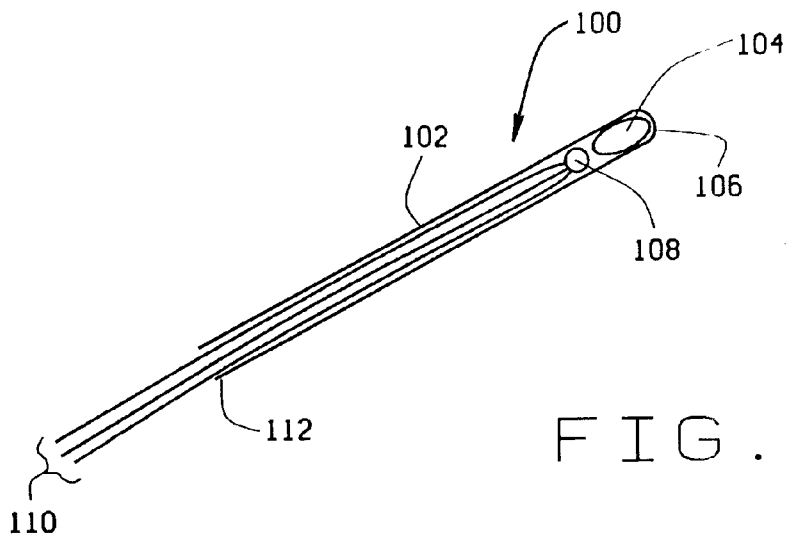
FIG. 1 is a perspective view of the magnetic probe of the present invention.

FIG. 1 is a diagram illustrating an embodiment 100 of an inventive device in accordance with a first aspect of the invention. This device comprises a flexible probe 102, which may be an endoscope or a catheter tube. A magnetic seed 104 of permanent magnetic, or at least a permeable material, is located near an end 106 of the flexible probe. Seed 104 preferably comprises a samarium-cobalt (SmCo) permanent magnet, or even more preferably a neodymium-boron-iron (NdBFe) permanent magnet. Typically, seed 104 may be about 0.7 mm in diameter and length, but may range up to about 4–5 mm in diameter and up to 7–10 mm long, depending upon the surgical application of probe 102. It is not intended to exclude seeds of other sizes, whether larger or smaller, from the scope of the invention. Preferably, seeds 104 of the sizes given as examples would have magnetic fields in the immediate vicinity of seed 104 of no more than 0.4 T. It is contemplated that the magnetic seed 104 is fixedly held in place in a suitable configuration inside or outside the probe, so that when the end 106 of probe 102 is implanted in a patient, an externally-applied magnetic field can be used to guide, direct and/or pull end 106 of probe 102 through a desired path in the patient's body by means of magnetic forces applied to seed 104, so that medicaments or therapy can be delivered to a selected location in the patient's body.

A magnetic field sensor.108, such as a 3-axis Hall effect probe, is also attached near the end 106 of probe 102, so that it is fixed in physical relationship to, and closely proximate magnetic seed 104 and the end of probe 102. Typically, the magnetic field from seed 104 at the location of sensor 108 would be about half of that indicated above in the immediate vicinity of the seed. Sensor or signal wires 110 from sensor 108 are led out an end 112 of probe 102 opposite end 106. Sensor wires 110 provide a signal or signals indicative of the magnitude and orientation of a magnetic field at or near the seed 104, and/or the end 106 of probe 102. If probe 102 is an endoscope, an optical fiber (not shown) may be provided to pass through the probe to provide a view of a region ahead of the endoscope. Other passages, not shown, may be provided for other surgical purposes.

Figure 2:
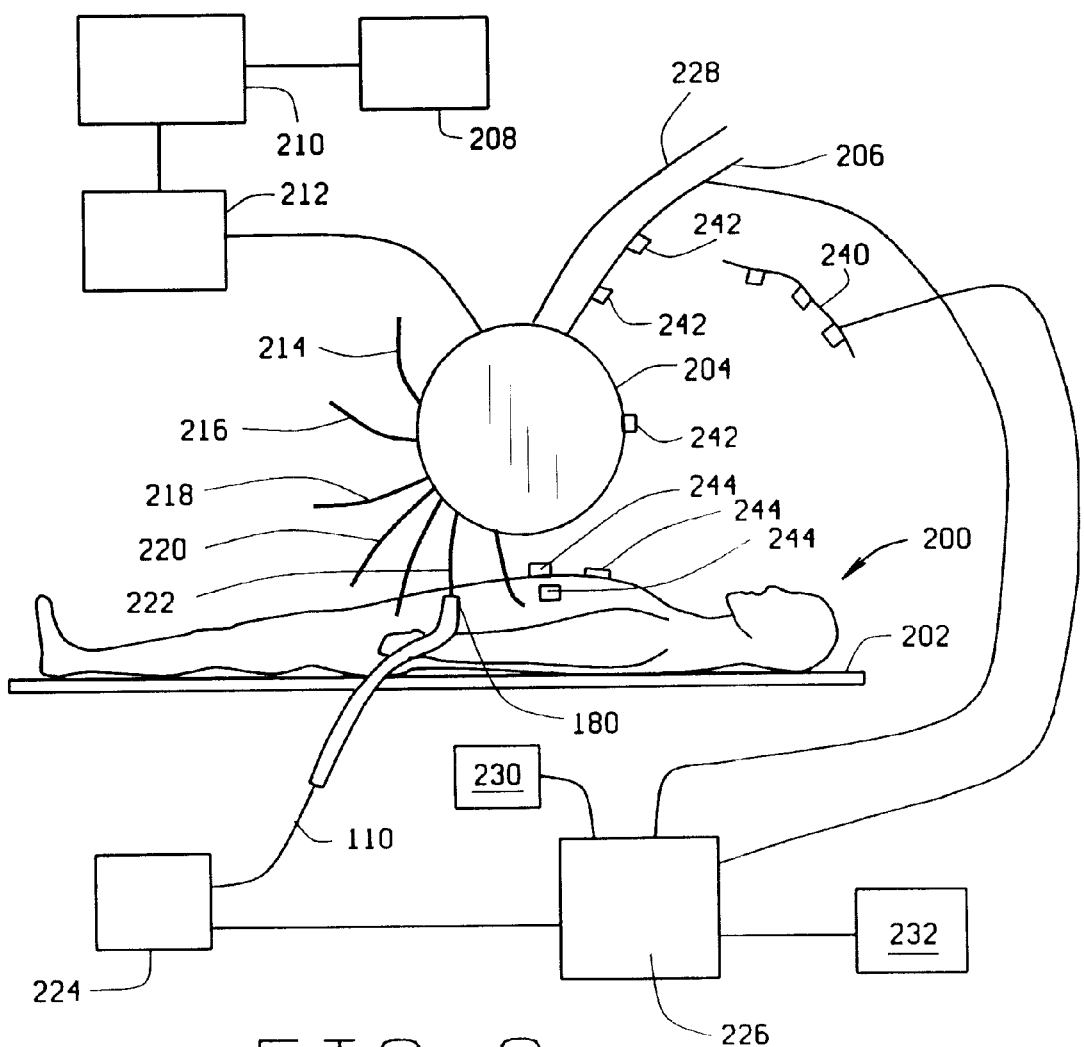
FIG. 2 is a perspective view of the field generating coil, along with equipment needed to use it for the location of the implant.

Referring now to FIG. 2, probe 102 is shown implanted in a patient 200 resting on a table 202. A calibrated electromagnet 204 generating a magnetic field having a known magnitude as a function of current, and having a known orientation as a function of location relative to electromagnet 204 is provided. Electromagnet 204 is used for locating implant 100, or more precisely, the field sensor 108 which is part of implant 100. Electromagnet 204 may also be used to generate forces or field lines that may be used to move or to guide the movement of implant 100 through patient 200. Electromagnet 204 may be attached to a moveable mounting arm 206 for this purpose. Typically, electromagnet 204 is capable of generating a field of between 0.1–0.3 T at the location of seed 104, or where it is intended that seed 104 is to be moved.

In a preferred configuration, a low frequency generator 208 provides a signal to a computer 210, which adds or mixes this signal with its own computation of the current required by electromagnet 204 to generate a magnetic field for purposes of guiding implant 100. This combined signal is sent to an amplifier/power supply 212, which provides current to electromagnet 204. Electromagnet 204 generates magnetic field lines such as 214, 216, 218, 220, and 222 shown in FIG. 2. Sensor 108 of implant 100 lies on one of these field lines, shown as 222 in FIG. 2, and sensor 108 senses the strength and direction of the field at the location of implant 100. Wires 110 from the probe travel through the probe 210 (which is usually an endoscope or catheter), to instrument module 224, which converts the signals to a magnetic field direction and magnitude as sensed by the probe. This information is sent to a computer 226, which may be, but need not be the same as computer 212. Computer 226 has also received information from mounting arm 228, which enables it to know the location and orientation of electromagnet 204. As long as no rotation of the magnet about its axis has occurred, there is no ambiguity of the field lines in question. For the front hemisphere of electromagnet 204, the field lines are known to computer 226 (for example, by having a representation thereof in a reference frame of the electromagnet 204 stored in a memory 230), so that the computer 226 can match the data received from instrument module 224 with data from the known field lines in memory 230, to determine the location and orientation of probe 106 relative to electromagnet 204. This information may be provided to a display 232, or it may be provided to computer 210 (or used by computer 210, if computers 226 and 210 are one and the same computer) to provide a signal to the magnet power supply 212 in a manner according to "Method and Apparatus Using Shaped Field of Repositionable Magnet to Guide Implant," U.S. Provisional Patent App. No. 60/065,103 to W. M. Blume et al., filed Nov. 12, 1997, and a non-provisional application by the same title as the provisional application, also to W. M. Blume et al., and filed on even date with the present application (both the provisional and non-provisional applications referred to being herein incorporated by reference in their entirety), or otherwise as may be known in the art.

The use of a modulated signal to generate the magnetic field of electromagnet 204 allows various signal processing methods known to those skilled in the art to achieve better accuracy in determining the location of probe 102. With such modulation, for example, it becomes less necessary, or unnecessary, to account for a varying DC current to electromagnet 204, which would otherwise have to be taken into account by computer 226 in correlating the measured magnitude of the field with the stored representation of the relationship of spacial locations to the magnetic field pattern produced by electromagnet 204 that is stored in memory 230. Of course, the varying DC current could be taken into account by communicating this information from computer 210 to computer 226, or if computers 210 and 226 are one and the same computer.

It is thus seen that, in this invention, a low frequency oscillating signal is added—electronically summed—into the signal from a computer that sets a current from the amplifier—power supplies to one or more coils. The present invention is used with a single field generating coil, although accurately known fields from any coil assembly could be used if they do not have duplicate fields at more than one location. The oscillating signal is detected by a very small 3-axis magnetic field sensor, for example a 3-axis Hall probe, attached to the magnetic implant. The signal wires for the probe are led out of the body by being in the catheter or endoscope which contains or is attached to the guided magnetic implant, and which is being moved in the body duct.

The three Hall voltages from the magnetic field sensor provide a direction and magnitude for the oscillating magnetic field at the location of the probe. The oscillating signals are separated from the contributions from the steady guiding field by the use of dc isolation or controlled biasing, and are made accurate by the well known technique of synchronous detection, or some other electronic noise reducing means. Since the desired guidance field is computer generated and the signal is then sent to the magnet power supply amplifier, this signal can easily be used to insert an appropriate biasing voltage in each of the three sensor leads so as not to overload sensitive synchronous detection (or other) circuitry for the locating function. The signal from the proximate magnetic seed will either be a DC signal (if the seed is a permanent magnet) that can be biased out, or an AC signal (if the seed is a permeable material) that introduces a known or calculable multiplicative factor that can be removed through simple techniques such as gain adjustment, if the seed is operated in its linear range of permeability. (More complicated corrections would be required if the seed is a permeable material operated at or near saturation, but it is not envisioned that such operation would normally be necessary.) The subsequent output from this circuitry becomes the functional locator signals, sent to analysis in the computer.

The locator signals from the magnetic field sensor, with the aid of the computer which has either a lookup table or other means to know the source magnet field pattern (in conjunction with knowledge of any deviation of the source magnet from its standard position and direction), provide a unique direction and magnitude of the oscillating magnetic field component of the source magnet, at the position of the probe, and as measured in the frame of the probe, based on its orientation. For the front half of the field generating magnet, for a given current there is a unique pattern of the magnetic field direction and strength. If this pattern is stored in the operating computer, then knowledge of a measured field at any location near the magnet would locate the point in relationship to the coil. If, in addition, the angle of the axis of the magnet is known to the computer, and the location of the coil center is known also, in relation to some fixed reference frame, then the computer, reading the signals from the implant, can provide the location and direction of the implant continuously in that reference frame. If the patient is located relative to that reference frame, then the implant position and direction is known relative to the patent. This can be accomplished, for example, by providing fiducial markers 242 and 244 on a patient's body and on the magnet and/or magnet arm and locators, as shown in FIG. 2, and by providing a localizer 240 to provide a signal representative of the location of these fiducial markers to processor 226. Processor 226 can then provide a correction to the locations sensed—i.e., provide spatial coordinates in the coordinate system of the room, rather than relative to the electromagnet 204, based upon the signals from localizer 240. The use of localizers is more fully described in U.S. Provisional Application No. 60/065,103, Filed Nov. 12, 1997, and incorporated by reference in its entirety above.

Thus, the invention provides a location and direction of the implant relative to the magnet, for the purpose of allowing correct orientation of the magnet to guide it in a desired direction, and a location and direction of the implant relative to the patient, which for some purposes can be useful to the physician in knowing where in a body duct the implant is located, without the need for real time imaging apparatus in place if that is not otherwise needed for medical purposes. It can also be envisioned, however, that some medically useful preoperative image of the patient could be put on a computer screen, and some icon of the implant superimposed on that image as the implant moves.

In another embodiment of the invention, a further use of the invention may be made in which information from instrument module or demodulator 224 is used on a display 232 and combined with preoperative images which may be supplied to computer 226 in some conventional way. There are many different locations around the front hemisphere of the electromagnet 204 which have the same field line directions, but these locations all differ in the magnitude of the field. As the field line leaving the magnet in a given plane, and from a more frontmost point bends, it can have the same direction that another field line had, in that plane, which left the magnet further back. But it will be further out as it reaches that angle, and the field will be weaker. This describes the nature of the magnetic field by which there is a unique field line pattern in each hemisphere of the magnet. (Preferably, electromagnet 204 will generate a hemispherically symmetrical field. If the magnet is not symmetric end-to-end, there will not be the hemispheric symmetry. Nevertheless, such magnets can be made to function in this invention by merely adapting the "map" of this field for use in the analysis.)

In the use of this invention, the location and orientation of the magnetometer probe, and hence the implant, is made available to the physician executing the procedure, and this location is made known using the same magnet (or perhaps magnets) as is used to guide the probe. This location can be made known and updated essentially simultaneously with the actual guidance of the probe. The physician can then know, for example, the direction of his vision in an endoscope with an optical fiber system viewing the region ahead of the endoscope.

When location information is displayed and combined with preoperative imaging, the system must be "calibrated" preoperatively, with some localizing method, such as has been described in "Method and Apparatus Using Shaped Field of Repositionable Magnet to Guide Implant," incorporated by reference in its entirety above. The display may be of any type useful for medical imaging. For example, the display could be a volume rendered MRI image, so that the seed can be located in its physiological context at each point of the path.

In use, the basic operation of the inventive apparatus is accomplished by a method comprising the steps of surgically implanting a magnetic implant 100 including an associated magnetic field probe 108 in a patient 200; applying a modulated magnetic field from a calibrated electromagnet 204; detecting signals from the magnetic probe resulting from the application of the modulated magnetic field using demodulator 224; and computing the relative location of the magnetic probe, and therefore, the magnetic implant, with respect to the electromagnet, from the detected signals from the magnetic probe. Optionally, the patient and electromagnet may be located with a localizer and an indication of the location of the magnetic probe relative to the patient may be displayed on a preoperative image of the patient with the indication of the location of the magnetic probe superimposed on the display.

Many modifications and variations of the inventive concept would be evident to one skilled in the art upon reading and understanding this disclosure, and the embodiments described herein are intended to be exemplary rather than exclusive. For these reasons, the scope of the invention should be determined with reference to the claims appended below, and the full legal range of equivalents permitted under applicable law.

What is claimed is:

1. A method for locating a magnetic surgical implant, comprising the steps of:
    (a) surgically implanting a magnetic implant including an associated magnetic field probe in a patient;
    (b) applying a modulated magnetic field from an external electromagnet;
    (c) detecting signals from the magnetic probe resulting from the application of the modulated magnetic field; and
    (d) computing the relative location of the magnetic probe, and therefore, the magnetic implant, with respect to the electromagnet, from the detected signals from the magnetic probe.

2. The method of claim 1, and further comprising the steps of locating the patient and electromagnet with a localizer and displaying an indication of the location of the magnetic probe relative to the patient on a display.

3. The method of claim 2, and further comprising the step of superimposing a preoperative image of the patient on the display with the indication of the location of the magnetic probe.

4. The method of claim 3 wherein the step of applying a modulated magnetic field from an external electromagnet comprises the steps of selecting a current required by the external electromagnet to guide the magnetic implant and modulating the selected current with a modulating signal;
    and further comprising the step of guiding the magnetic probe with the modulated magnetic field.

5. The method of claim 1 wherein the step of applying a modulated magnetic field from an external electromagnet comprises the steps of selecting a current required by the external electromagnet to guide the magnetic implant and modulating the selected current with a modulating signal;
    and further comprising the step of guiding the magnetic probe with the modulated magnetic field.

* * * * *